(12) United States Patent
Uvnäs-Moberg et al.

(10) Patent No.: US 12,402,621 B2
(45) Date of Patent: Sep. 2, 2025

(54) METHOD FOR INCREASING LONGEVITY AND/OR BUD OPENING OF CUT FLOWERS

(71) Applicant: LETAVIS AB, Stockholm (SE)

(72) Inventors: Kerstin Uvnäs-Moberg, Djursholm (SE); Bengt Lundegårdh, Uppsala (SE)

(73) Assignee: LETAVIS AB, Älta (SE)

( * ) Notice: Subject to any disclaimer, the term of this patent is extended or adjusted under 35 U.S.C. 154(b) by 708 days.

(21) Appl. No.: 17/776,740

(22) PCT Filed: Dec. 18, 2020

(86) PCT No.: PCT/EP2020/087068
§ 371 (c)(1),
(2) Date: May 13, 2022

(87) PCT Pub. No.: WO2021/123201
PCT Pub. Date: Jun. 24, 2021

(65) Prior Publication Data
US 2022/0408722 A1    Dec. 29, 2022

(30) Foreign Application Priority Data
Dec. 18, 2019    (SE) .................................... 1951489-2

(51) Int. Cl.
*A01N 3/02*    (2006.01)
*C07K 7/16*    (2006.01)

(52) U.S. Cl.
CPC . *A01N 3/02* (2013.01); *C07K 7/16* (2013.01)

(58) Field of Classification Search
CPC .................................... A01N 3/02; C07K 7/16
See application file for complete search history.

(56) References Cited

FOREIGN PATENT DOCUMENTS

WO    WO 02/102160 A1    12/2002

OTHER PUBLICATIONS

De L.C., et al., Effect of Chemicals for Tight Bud Opening of Rose Cv. 'Super Star' at Different Stages of Maturity, Annals of Agricultural Science, vol. 20, Jun. 30, 1999, pp. 206-211.
International Search Report and Written Opinion mailed on Mar. 31, 2021 by the International Searching Authority for International Application No. PCT/EP2020/087068 filed on Dec. 18, 2020 and published as WO 2021/123201 (Applicant—Letavis AB) (9 pages).

*Primary Examiner* — David Browe
(74) *Attorney, Agent, or Firm* — Ballard Spahr LLP

(57) ABSTRACT

Disclosed is a method for increasing the bud opening and/or longevity of cut flowers by exposing the cut flowers to an oxytocin solution and/or a variant and/or derivative thereof.

17 Claims, 12 Drawing Sheets
Specification includes a Sequence Listing.

```
                      SEQUENCE LISTING

<160> NUMBER OF SEQ ID NOS: 24

<210> SEQ ID NO 1
<211> LENGTH: 9
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: AMIDATION

<400> SEQUENCE: 1

Cys Tyr Ile Gln Asn Cys Pro Leu Gly
1               5

<210> SEQ ID NO 2
<211> LENGTH: 10
<212> TYPE: PRT
<213> ORGANISM: Artificial sequence
<220> FEATURE:
<223> OTHER INFORMATION: Oxytocin fragments and variants
<220> FEATURE:
<221> NAME/KEY: MISC_FEATURE
<222> LOCATION: (1)..(1)
<223> OTHER INFORMATION: X1 can be Cys or nothing
<220> FEATURE:
<221> NAME/KEY: MISC_FEATURE
<222> LOCATION: (2)..(2)
<223> OTHER INFORMATION: X2 can be Tyr, Phe or nothing
<220> FEATURE:
<221> NAME/KEY: MISC_FEATURE
<222> LOCATION: (3)..(3)
<223> OTHER INFORMATION: X3 can be Ile, Val, Hoph, Phe, Cha or nothing
<220> FEATURE:
<221> NAME/KEY: MISC_FEATURE
<222> LOCATION: (4)..(4)
<223> OTHER INFORMATION: X4 can be Gln, Ser, Thr, Cit, Arg or Daba
<220> FEATURE:
<221> NAME/KEY: MISC_FEATURE
<222> LOCATION: (7)..(7)
<223> OTHER INFORMATION: X5 (position 7) can be Pro or nothing
<220> FEATURE:
```

```
<221> NAME/KEY: MISC_FEATURE
<222> LOCATION: (8)..(8)
<223> OTHER INFORMATION: X6 (position 8) can be Ile, Leu, nothing, Val,
      Hos, Daba, Thr, Arg or Cit
<220> FEATURE:
<221> NAME/KEY: MISC_FEATURE
<222> LOCATION: (9)..(9)
<223> OTHER INFORMATION: X7 (position 9) can be Gly, nothing or Ala
<220> FEATURE:
<221> NAME/KEY: MOD_RES
<222> LOCATION: (10)..(10)
<223> OTHER INFORMATION: AMIDATION
<220> FEATURE:
<221> NAME/KEY: MISC_FEATURE
<222> LOCATION: (10)..(10)
<223> OTHER INFORMATION: X8 (position 10) can be Gly or nothing

<400> SEQUENCE: 2

Xaa Xaa Xaa Xaa Asn Cys Xaa Xaa Xaa Xaa
 1               5                  10

<210> SEQ ID NO 3
<211> LENGTH: 9
<212> TYPE: PRT
<213> ORGANISM: Bird
<220> FEATURE:
<221> NAME/KEY: MOD_RES
<222> LOCATION: (9)..(9)
<223> OTHER INFORMATION: AMIDATION

<400> SEQUENCE: 3

Cys Tyr Ile Gln Asn Cys Pro Ile Gly
 1               5

<210> SEQ ID NO 4
<211> LENGTH: 9
<212> TYPE: PRT
<213> ORGANISM: Fish
<220> FEATURE:
<221> NAME/KEY: MOD_RES
<222> LOCATION: (9)..(9)
<223> OTHER INFORMATION: AMIDATION

<400> SEQUENCE: 4

Cys Tyr Ile Ser Asn Cys Pro Ile Gly
 1               5

<210> SEQ ID NO 5
<211> LENGTH: 9
<212> TYPE: PRT
<213> ORGANISM: Eisenia foetida
<220> FEATURE:
<221> NAME/KEY: MOD_RES
<222> LOCATION: (9)..(9)
<223> OTHER INFORMATION: AMIDATION

<400> SEQUENCE: 5

Cys Phe Val Arg Asn Cys Pro Thr Gly
 1               5

<210> SEQ ID NO 6
<211> LENGTH: 9
<212> TYPE: PRT
<213> ORGANISM: unknown
<220> FEATURE:
<223> OTHER INFORMATION: non-mammalian vertebrates, fetal mammals
<220> FEATURE:
<221> NAME/KEY: MOD_RES
<222> LOCATION: (9)..(9)
<223> OTHER INFORMATION: AMIDATION
```

```
<400> SEQUENCE: 6

Cys Tyr Ile Gln Asn Cys Pro Arg Gly
1               5

<210> SEQ ID NO 7
<211> LENGTH: 9
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: AMIDATION

<400> SEQUENCE: 7

Cys Tyr Phe Gln Asn Cys Pro Arg Gly
1               5

<210> SEQ ID NO 8
<211> LENGTH: 6
<212> TYPE: PRT
<213> ORGANISM: Artificial sequence
<220> FEATURE:
<223> OTHER INFORMATION: Oxytocin fragment
<220> FEATURE:
<221> NAME/KEY: MOD_RES
<222> LOCATION: (6)..(6)
<223> OTHER INFORMATION: AMIDATION

<400> SEQUENCE: 8

Cys Tyr Ile Gln Asn Cys
1               5

<210> SEQ ID NO 9
<211> LENGTH: 7
<212> TYPE: PRT
<213> ORGANISM: Artificial sequence
<220> FEATURE:
<223> OTHER INFORMATION: oxytocin fragment
<220> FEATURE:
<221> NAME/KEY: MOD_RES
<222> LOCATION: (7)..(7)
<223> OTHER INFORMATION: AMIDATION

<400> SEQUENCE: 9

Cys Tyr Ile Gln Asn Cys Pro
1               5

<210> SEQ ID NO 10
<211> LENGTH: 8
<212> TYPE: PRT
<213> ORGANISM: Artificial sequence
<220> FEATURE:
<223> OTHER INFORMATION: Oxytocin fragment
<220> FEATURE:
<221> NAME/KEY: MOD_RES
<222> LOCATION: (8)..(8)
<223> OTHER INFORMATION: AMIDATION

<400> SEQUENCE: 10

Cys Tyr Ile Gln Asn Cys Pro Leu
1               5

<210> SEQ ID NO 11
<211> LENGTH: 8
<212> TYPE: PRT
<213> ORGANISM: Artificial sequence
<220> FEATURE:
<223> OTHER INFORMATION: Oxytocin fragment
<220> FEATURE:
```

```
<221> NAME/KEY: MOD_RES
<222> LOCATION: (8)..(8)
<223> OTHER INFORMATION: AMIDATION

<400> SEQUENCE: 11

Tyr Ile Gln Asn Cys Pro Leu Gly
1               5

<210> SEQ ID NO 12
<211> LENGTH: 7
<212> TYPE: PRT
<213> ORGANISM: Artificial sequence
<220> FEATURE:
<223> OTHER INFORMATION: Oxytocin fragment
<220> FEATURE:
<221> NAME/KEY: MOD_RES
<222> LOCATION: (7)..(7)
<223> OTHER INFORMATION: AMIDATION

<400> SEQUENCE: 12

Ile Gln Asn Cys Pro Leu Gly
1               5

<210> SEQ ID NO 13
<211> LENGTH: 6
<212> TYPE: PRT
<213> ORGANISM: Artificial sequence
<220> FEATURE:
<223> OTHER INFORMATION: Oxytocin fragment
<220> FEATURE:
<221> NAME/KEY: MOD_RES
<222> LOCATION: (6)..(6)
<223> OTHER INFORMATION: AMIDATION

<400> SEQUENCE: 13

Gln Asn Cys Pro Leu Gly
1               5

<210> SEQ ID NO 14
<211> LENGTH: 5
<212> TYPE: PRT
<213> ORGANISM: Artificial sequence
<220> FEATURE:
<223> OTHER INFORMATION: Oxytocin fragment
<220> FEATURE:
<221> NAME/KEY: MOD_RES
<222> LOCATION: (5)..(5)
<223> OTHER INFORMATION: AMIDATION

<400> SEQUENCE: 14

Ile Gln Asn Cys Pro
1               5

<210> SEQ ID NO 15
<211> LENGTH: 10
<212> TYPE: PRT
<213> ORGANISM: Artificial sequence
<220> FEATURE:
<223> OTHER INFORMATION: Oxytocin variant
<220> FEATURE:
<221> NAME/KEY: MOD_RES
<222> LOCATION: (10)..(10)
<223> OTHER INFORMATION: AMIDATION

<400> SEQUENCE: 15

Cys Tyr Ile Gln Asn Cys Pro Leu Gly Gly
1               5                   10

<210> SEQ ID NO 16
```

```
<211> LENGTH: 6
<212> TYPE: PRT
<213> ORGANISM: Artificial sequence
<220> FEATURE:
<223> OTHER INFORMATION: Oxytocin variant
<220> FEATURE:
<221> NAME/KEY: MOD_RES
<222> LOCATION: (6)..(6)
<223> OTHER INFORMATION: AMIDATION

<400> SEQUENCE: 16

Gln Asn Cys Pro Leu Leu
1               5

<210> SEQ ID NO 17
<211> LENGTH: 9
<212> TYPE: PRT
<213> ORGANISM: Artificial sequence
<220> FEATURE:
<223> OTHER INFORMATION: Oxytocin variant
<220> FEATURE:
<221> NAME/KEY: MOD_RES
<222> LOCATION: (9)..(9)
<223> OTHER INFORMATION: AMIDATION

<400> SEQUENCE: 17

Cys Tyr Val Thr Asn Cys Pro Leu Gly
1               5

<210> SEQ ID NO 18
<211> LENGTH: 9
<212> TYPE: PRT
<213> ORGANISM: Artificial sequence
<220> FEATURE:
<223> OTHER INFORMATION: Oxytocin variant
<220> FEATURE:
<221> NAME/KEY: MISC_FEATURE
<222> LOCATION: (3)..(3)
<223> OTHER INFORMATION: X is Hoph
<220> FEATURE:
<221> NAME/KEY: MOD_RES
<222> LOCATION: (9)..(9)
<223> OTHER INFORMATION: AMIDATION

<400> SEQUENCE: 18

Cys Tyr Xaa Thr Asn Cys Pro Val Gly
1               5

<210> SEQ ID NO 19
<211> LENGTH: 9
<212> TYPE: PRT
<213> ORGANISM: Artificial sequence
<220> FEATURE:
<223> OTHER INFORMATION: Oxytocin variant
<220> FEATURE:
<221> NAME/KEY: MISC_FEATURE
<222> LOCATION: (4)..(4)
<223> OTHER INFORMATION: X is Cit
<220> FEATURE:
<221> NAME/KEY: MOD_RES
<222> LOCATION: (9)..(9)
<223> OTHER INFORMATION: AMIDATION

<400> SEQUENCE: 19

Cys Tyr Phe Xaa Asn Cys Pro Leu Gly
1               5

<210> SEQ ID NO 20
<211> LENGTH: 9
<212> TYPE: PRT
<213> ORGANISM: Artificial sequence
```

```
<220> FEATURE:
<223> OTHER INFORMATION: Oxytocin variant
<220> FEATURE:
<221> NAME/KEY: MISC_FEATURE
<222> LOCATION: (3)..(3)
<223> OTHER INFORMATION: X is Cha
<220> FEATURE:
<221> NAME/KEY: MISC_FEATURE
<222> LOCATION: (8)..(8)
<223> OTHER INFORMATION: X is Hos
<220> FEATURE:
<221> NAME/KEY: MOD_RES
<222> LOCATION: (9)..(9)
<223> OTHER INFORMATION: AMIDATION

<400> SEQUENCE: 20

Cys Tyr Xaa Arg Asn Cys Pro Xaa Ala
1               5

<210> SEQ ID NO 21
<211> LENGTH: 9
<212> TYPE: PRT
<213> ORGANISM: Artificial sequence
<220> FEATURE:
<223> OTHER INFORMATION: Oxytocin variant
<220> FEATURE:
<221> NAME/KEY: MISC_FEATURE
<222> LOCATION: (4)..(4)
<223> OTHER INFORMATION: X is Daba
<220> FEATURE:
<221> NAME/KEY: MISC_FEATURE
<222> LOCATION: (8)..(8)
<223> OTHER INFORMATION: X is Daba
<220> FEATURE:
<221> NAME/KEY: MOD_RES
<222> LOCATION: (9)..(9)
<223> OTHER INFORMATION: AMIDATION

<400> SEQUENCE: 21

Cys Tyr Val Xaa Asn Cys Pro Xaa Ala
1               5

<210> SEQ ID NO 22
<211> LENGTH: 9
<212> TYPE: PRT
<213> ORGANISM: Artificial sequence
<220> FEATURE:
<223> OTHER INFORMATION: Oxytocin variant
<220> FEATURE:
<221> NAME/KEY: MISC_FEATURE
<222> LOCATION: (3)..(3)
<223> OTHER INFORMATION: X is Hoph
<220> FEATURE:
<221> NAME/KEY: MISC_FEATURE
<222> LOCATION: (4)..(4)
<223> OTHER INFORMATION: X is Daba
<220> FEATURE:
<221> NAME/KEY: MISC_FEATURE
<222> LOCATION: (8)..(8)
<223> OTHER INFORMATION: X is Cit
<220> FEATURE:
<221> NAME/KEY: MOD_RES
<222> LOCATION: (9)..(9)
<223> OTHER INFORMATION: AMIDATION

<400> SEQUENCE: 22

Cys Tyr Xaa Xaa Asn Cys Pro Xaa Ala
1               5

<210> SEQ ID NO 23
<211> LENGTH: 9
<212> TYPE: PRT
<213> ORGANISM: Artificial sequence
```

```
<220> FEATURE:
<223> OTHER INFORMATION: Oxytocin variant
<220> FEATURE:
<221> NAME/KEY: MOD_RES
<222> LOCATION: (9)..(9)
<223> OTHER INFORMATION: AMIDATION

<400> SEQUENCE: 23

Cys Tyr Phe Arg Asn Cys Pro Val Ala
1               5

<210> SEQ ID NO 24
<211> LENGTH: 9
<212> TYPE: PRT
<213> ORGANISM: Artificial sequence
<220> FEATURE:
<223> OTHER INFORMATION: Oxytocin variant
<220> FEATURE:
<221> NAME/KEY: MISC_FEATURE
<222> LOCATION: (3)..(3)
<223> OTHER INFORMATION: X is Cha
<220> FEATURE:
<221> NAME/KEY: MISC_FEATURE
<222> LOCATION: (4)..(4)
<223> OTHER INFORMATION: X is Cit
<220> FEATURE:
<221> NAME/KEY: MOD_RES
<222> LOCATION: (9)..(9)
<223> OTHER INFORMATION: AMIDATION

<400> SEQUENCE: 24

Cys Tyr Xaa Xaa Asn Cys Pro Arg Gly
1               5
```

METHOD FOR INCREASING LONGEVITY AND/OR BUD OPENING OF CUT FLOWERS

CROSS-REFERENCE TO RELATED APPLICATIONS

This application is a U.S. National Phase Application of International Application No. PCT/EP2020/087068, filed Dec. 18, 2020, which claims priority to Swedish Application No. 1951489-2, filed Dec. 18, 2019, each of which are hereby incorporated by reference in their entirety.

REFERENCE TO SEQUENCE LISTING

The Sequence Listing submitted May 17, 2022 as a text file named "38202_0002U1_Updated_Sequence_Listing.txt," created on May 17, 2022, and having a size of 43,748 bytes is hereby incorporated by reference pursuant to 37 C.F.R. § 1.52(e)(5).

TECHNICAL FIELD

The present document is directed to the field of agriculture and to a method for increasing the bud opening and/or longevity of cut flowers.

BACKGROUND

The availability of cut flowers has increased as the possibilities of transporting the flowers a long way have been improved. However, cut flowers are highly perishable products with a very short life-cycle, therefore efficient logistics and processes along the supply-chain, from origin to destination are of very high importance to ensure speedy deliveries of flowers with preserved quality. According to the Union fleurs—international flower association, cut flowers lose 15% in value per extra-day in the supply chain.

Hence, there is a need and demand of an increased longevity of cut flowers. Further, cut flowers are usually harvested before the bud(s) open. A common problem with cut flowers is that the buds do not open fully or not at all, leading to a less appealing appearance of the flowers.

There is thus a need for providing improved means for increasing the longevity and/or bud opening of cut flowers.

SUMMARY

An object of the present is to provide improved means for increasing the longevity, freshness and/or bud opening of cut flowers.

The present document is thus directed to a method for increasing the bud opening and/or longevity of cut flowers, said method comprising
a) providing a solution comprising oxytocin, such as an aqueous oxytocin solution;
b) exposing the ends of the stems of said cut flowers to said solution.

The concentration of oxytocin may be about 0.05 to about 30 µM, such as about 0.05 to about 20 µM, such as about 0.1 to about 20 µM, such as about 0.5 to about 20 µM, such as about 1 to about 20 µM, such as about 5 to about 20 µM, such as about 5 to about 15 µM or about 10 µM.

The cut flowers may be exposed to the solution comprising oxytocin for a time period of about at least 6 hours, such as about 6 hours to about 30 days, about 6 hours to about 20 days, about 6 hours to about 19 days, about 1 day to about 19 days, about 3 days to about 19 days, such as about 1, 2, 3, 4, 5, 6, 7, 8, 9, 10, 11, 12, 13, 14, 15, 16, 17, 18, 19, or 20 days.

The cut flowers may be exposed to the solution comprising oxytocin at a temperature of from about 1 to about 25° C. such as from about 1 to about 20° C., from about 1 to about 15° C., from about 1 to about 10° C., from 5 to about 10° C., from about 10 to about 15° C., from about 20 to about 25° C. or from about 20 to about 22° C.

The solution comprising oxytocin may have a pH of from about 1 to about 9, such as from about 2 to about 8, from about 2 to about 7, from about 2 to about 6, from about 2 to about 5, from about 2 to about 4, from about 3 to about 5, from about 3 to about 4, such as about, 1, 2, 3, 4, 5, 6, 7, 8, or 9.

The method may be performed the first time the stems of the cut flowers are exposed to water after harvesting.

The cut flowers may be roses.

Instead of using oxytocin (SEQ ID NO:1), or in addition to using oxytocin, it is possible to use a fragment and/or variant of oxytocin according to SEQ ID NO:2 possessing oxytocin activity,
wherein SEQ ID NO:2 is

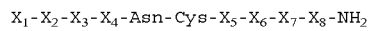

wherein
$X_1$ is selected from the group consisting of Cys and nothing;
$X_2$ is selected from the group consisting of Tyr, Phe, and nothing;
$X_3$ is selected from the group consisting of Ile, Val, Hoph, Phe, Cha, and nothing;
$X_4$ is selected from the group consisting of Gln, Ser, Thr, Cit, Arg, and Daba;
$X_5$ is selected from the group consisting of Pro and nothing;
$X_6$ is selected from the group consisting of Ile, Leu, nothing, Val, Hos, Daba, Thr, Arg, and Cit;
$X_7$ is selected from the group consisting of Gly, nothing, and Ala;
$X_8$ is selected from the group consisting of Gly and nothing.

The present document also provides the use of a solution comprising oxytocin and/or a fragment and/or variant thereof as described herein for increasing the longevity and/or bud opening of cut flowers.

Other features and advantages of the invention will be apparent from the following detailed description, drawings, examples, and from the claims.

Definitions

In the context of the present document, the term "longevity" in expressions like "increasing the longevity of cut flowers", "increased longevity of cut flowers" and the like, it is meant increasing the time the cut flower looks fresh, i.e. the time before the cut flower withers. This may include increasing the freshness of the cut flower, i.e. the time the flower looks fresh, e.g. the time the petals, sepals and/or leaves look fresh.

By "bud opening" is in the context of the present document intended the opening of the bud(s) of a cut flower. By the term "increasing the bud opening" it is in the context of the present document intended that the number of buds which open increases, that the buds open more fully, that the open flower(s) become(s) bigger, and/or that the petals and/or sepals look more appealing.

By "cut flower", "cut flowers" and the like is in the context of the present document intended flowering cut flowers as well as ornamental leaves, i.e. all kinds of plants typically used in bouquets.

With the term "oxytocin" in the context of the present document is intended oxytocin having the following chemical structure.

(SEQ ID NO: 1)

Cys—Tyr—Ile—Gln—Asn—Cys—Pro—Leu—Gly—NH$_2$

Whenever "oxytocin" is mentioned in the present document, this term is also understood to encompass a fragment and/or a variant (such as a homologue) of oxytocin that encompasses a biological activity comparable to the oxytocin molecule itself (SEQ ID NO:1).

Accordingly, a "variant" of oxytocin as referred to herein, refers to a peptide which has been varied in its amino acid structure as compared to the oxytocin molecule in that some amino acid positions may have been altered by introducing other amino acids in such positions, such as natural or unnatural amino acids as exemplified herein, or it may have been extended by adding one or more natural or unnatural amino acid(s) to either ends of the peptide. In addition, other structural variations may also have been performed to the present peptides as referred to herein, such as synthetic modifications. Said "variant" still maintains a biological activity similar to oxytocin and said oxytocin variant is also stabilized by being present in a pharmaceutical composition according to the present invention.

Furthermore, a "fragment" of oxytocin, as referred to herein is a peptide which comprises a part of the amino acid sequence of oxytocin, but wherein one or more amino acids may have been removed from one or both of the amino acid terminal end(s). This term also refers to a fragment of an oxytocin variant as defined in SEQ ID NO:2, hence meaning that also encompassed by the present invention is any fragment of a peptide as presented by SEQ ID NO:2.

Thus, as used herein, a fragment and/or variant of oxytocin according to SEQ ID NO:2 is understood to be

$X_1$-$X_2$-$X_3$-$X_4$-Asn-Cys-$X_5$-$X_6$-$X_7$-$X_8$-NH$_2$ wherein $X_1$ is selected from the group consisting of Cys and nothing;

$X_2$ is selected from the group consisting of Tyr, Phe, and nothing;

$X_3$ is selected from the group consisting of Ile, Val, Hoph, Phe, Cha, and nothing;

$X_4$ is selected from the group consisting of Gln, Ser, Thr, Cit, Arg, and Daba;

$X_5$ is selected from the group consisting of Pro and nothing;

$X_6$ is selected from the group consisting of Ile, Leu, nothing, Val, Hos, Daba, Thr, Arg, and Cit;

$X_7$ is selected from the group consisting of Gly, nothing, and Ala;

$X_8$ is selected from the group consisting of Gly and nothing.

The unnatural amino acids mentioned above have the following structures:

Cyclohexylalanine, herein referred to as Cha,

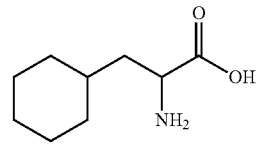 [SMILES: NC(CC1CCCCC1)C(=O)O]

Homophenylalanine, herein referred to as Hoph,

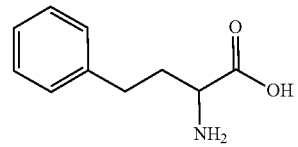 [SMILES: NC(CCc1ccccc1)C(=O)O]

Citrulline, herein referred to as Cit,

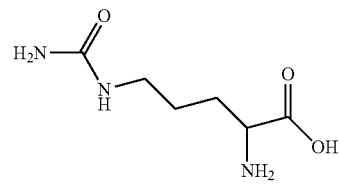 [SMILES: NC(=O)NCCCC(N)C(=O)O]

Diaminobutyric acid, herein referred to as Daba, and

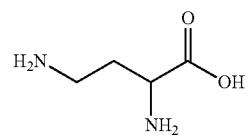

Homoserine, herein referred to as Hos,

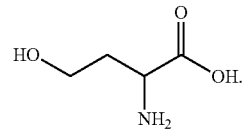

Figure 1:
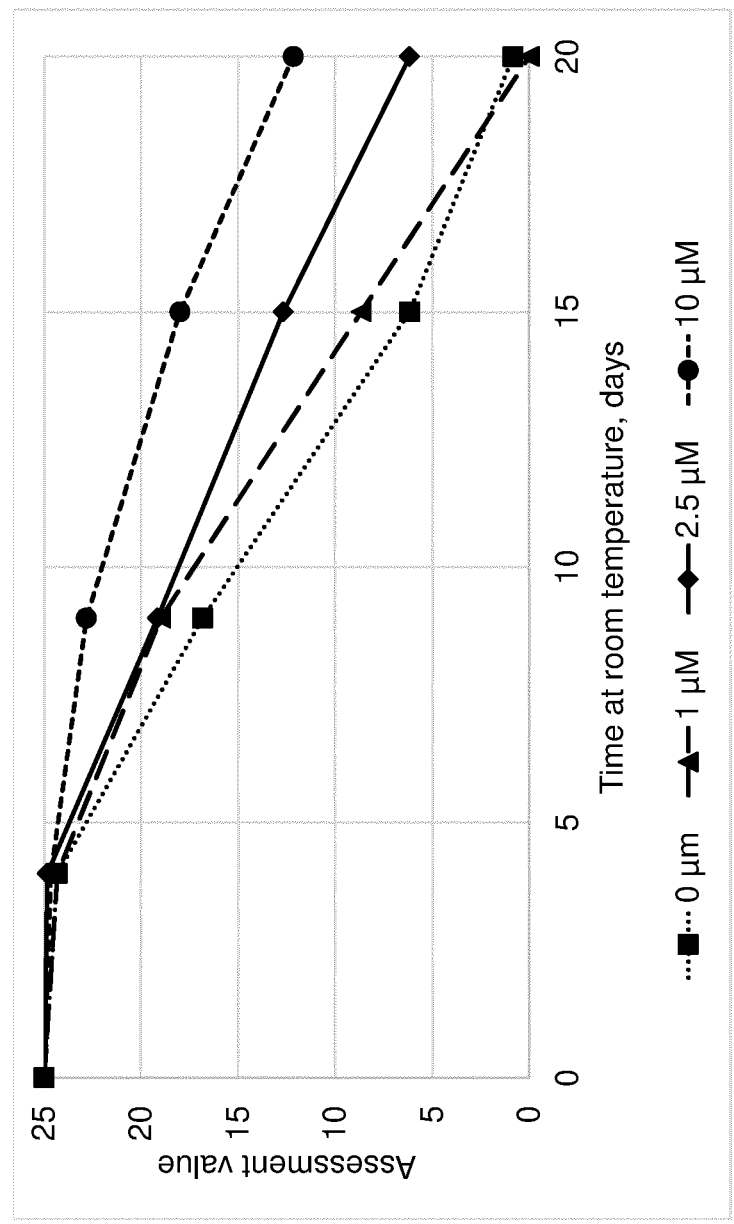
FIG. 1 shows the sum of different assessment scores for roses of the type Upper Class, which had been treated with oxytocin in a concentration of 0, 1, 2.5 or 10 µM in a cold room, at a time point of 4, 9, 15 and 20 days after being put in fresh tap water and moved to a home-like setting, as described in Example 1.
Figure 2A:
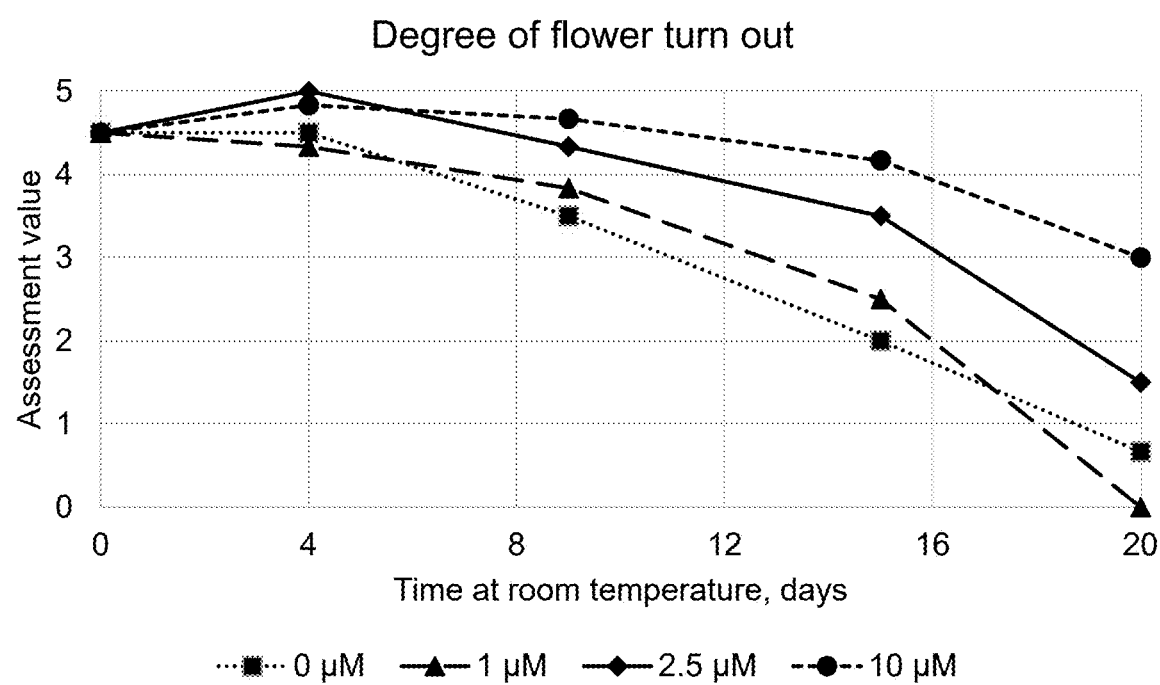
FIGS. 2A-2E show the mean score for each criterion for roses of the type Upper Class, which had been treated with oxytocin in a concentration of 0, 1, 2.5 or 10 µM of oxytocin in a cold room, at a time point of 4, 9, 15 and 20 days after being put in fresh tap water and moved to a home-like setting, as described in Example 1.
Figure 2B:
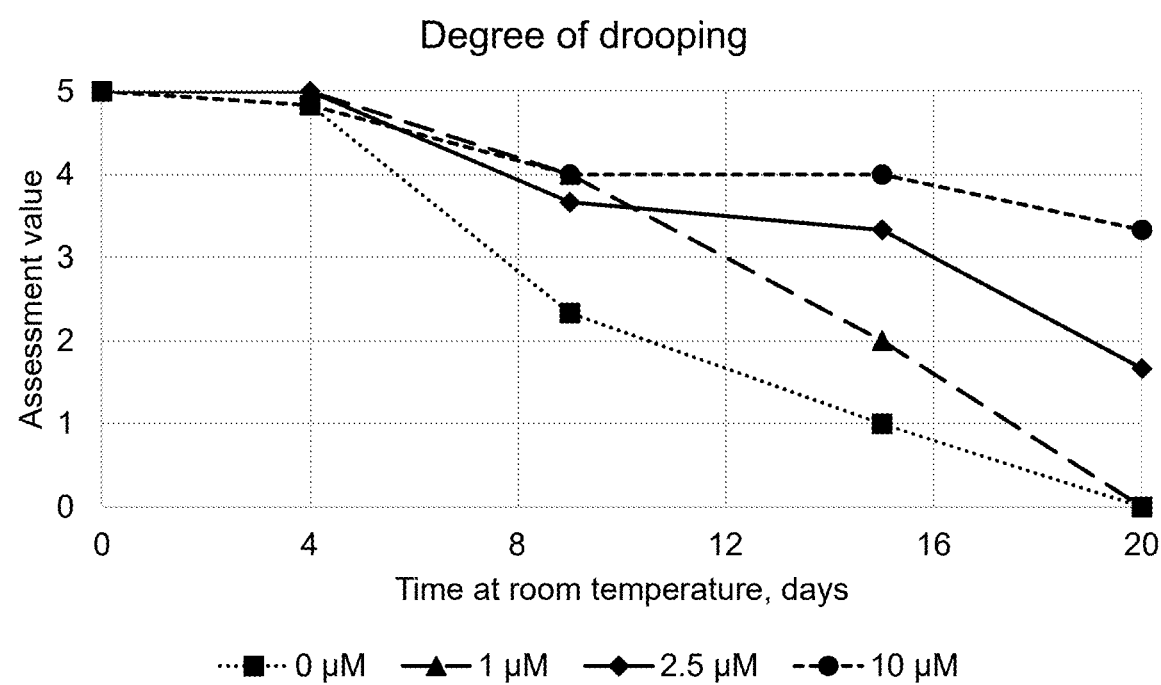
Figure 2C:
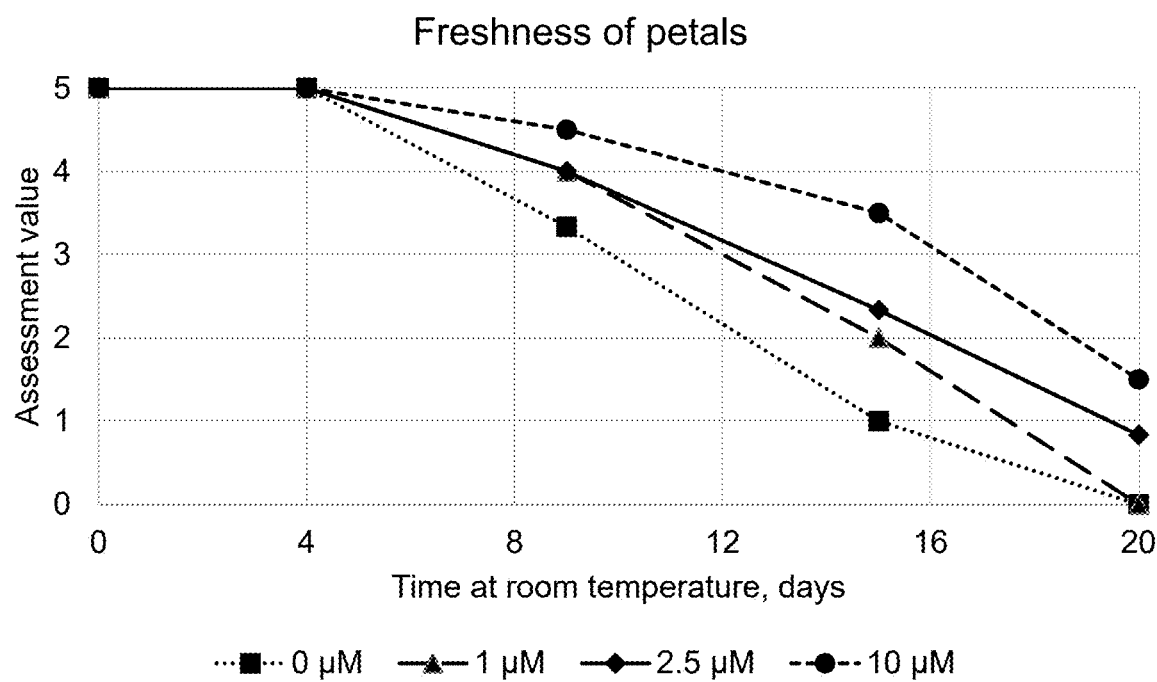
Figure 2D:
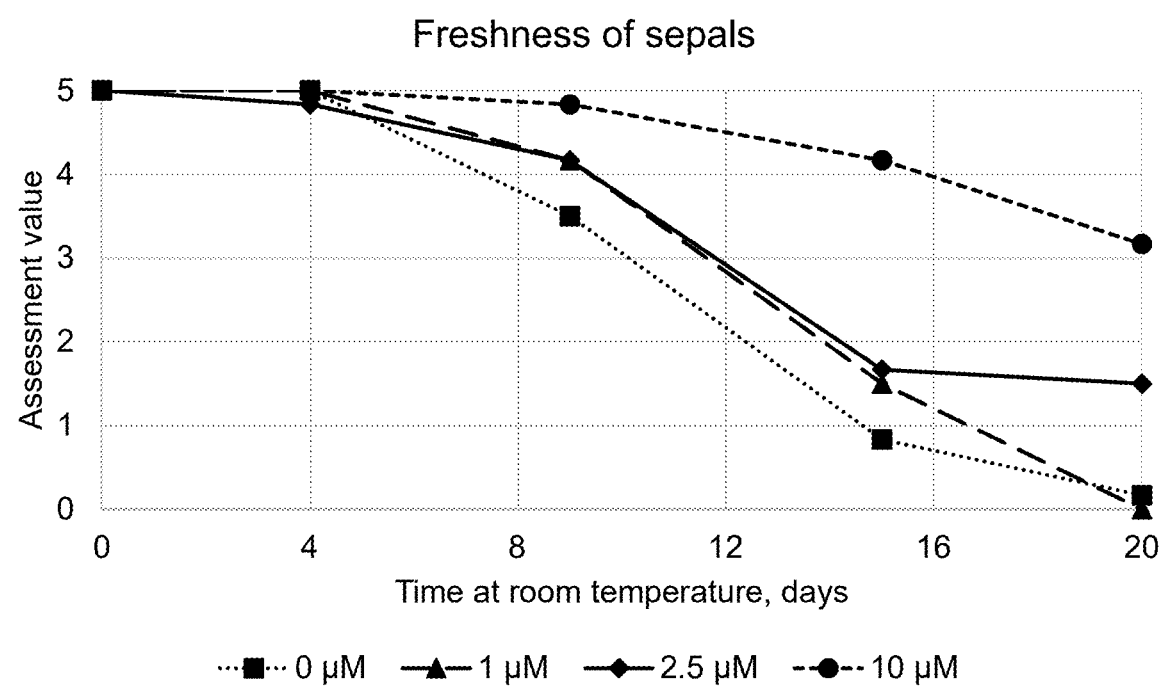
Figure 2E:
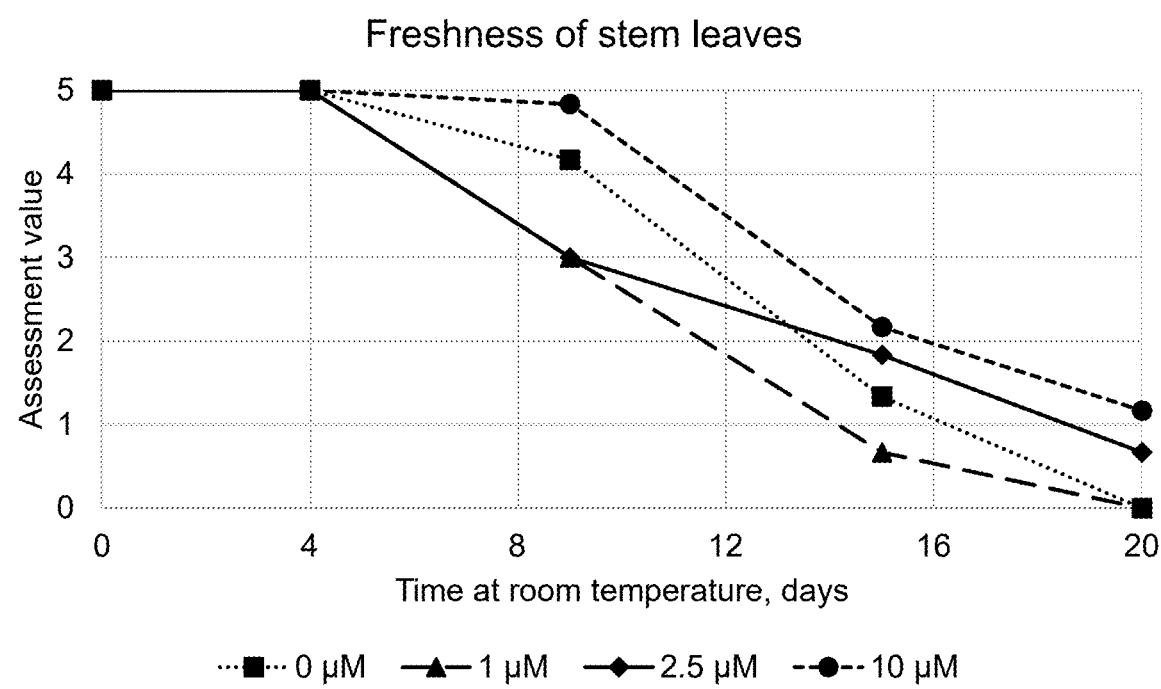

In this document, normal room temperature intends a temperature within the range of from about 20° C. to about 25° C.

DETAILED DESCRIPTION

The present inventors have surprisingly found that oxytocin can be used to increase the bud opening and/or longevity of cut flowers after they are harvested by exposing the cut flowers to oxytocin.

The present document thus discloses a for method for increasing the bud opening and/or longevity of cut flowers, said method comprising
  a) providing a solution comprising oxytocin, such as an aqueous oxytocin solution;
  b) exposing the ends of the stems of said cut flowers to said solution.

An increased longevity signifies that cut flowers' life cycle, such as highly perishable cut flowers' life cycle, is prolonged, e.g. the cut flowers remain aesthetically appealing for a longer time period and/or to a greater extent. An increased longevity may be manifested in that the petals, sepals and/or leaves of the cut flower look fresher or stay fresh for a longer time period. Further, an increased longevity may be shown as that the degree of or the number of flowers that are bent decreases (i.e. less drooping). The use of oxytocin thus increases the time until the cut flower withers.

An increased bud opening may for example mean that more of the buds of the flowers open and/or that the buds open more fully, that the open flower becomes bigger, and/or that the petals and/or sepals look more appealing.

The cut flowers are typically exposed to the solution comprising oxytocin by placing the cut flowers into said solution so that at least the cut end of the stem is covered by the solution comprising oxytocin.

The cut flowers may be exposed to a solution comprising oxytocin by immersing the cut flowers' in the solution comprising oxytocin the first time they are put in water after harvesting and/or at a later time point. Within the commercial trade of cut flowers, cut flowers are in general freeze-dried direct upon harvesting and/or stored in a cold place for transport and not put into water until later. Putting the cut flowers in a solution comprising oxytocin the first time the cut flowers are put into water after harvesting, which may thus be seen as a pre-treatment, results in an increased longevity of the cut flower as demonstrated in the experimental section. Alternatively or additionally, it is also possible to expose the cut flowers to a solution comprising oxytocin at later stages of the cut flowers' life cycle and thus achieve an increased longevity.

Thus, the cut flowers may be immersed in a solution comprising oxytocin at any time point during the supply chain until they are discarded. It may be preferred to at least perform the method the first time the stems of said cut flowers are exposed to water after harvesting and/or freeze-drying.

The cut flowers are typically exposed to the solution comprising oxytocin for a time period of at least 1 hour, such as at least 5 hours, such as at least 6 hours, such as about 6 hours to about 30 days, about 6 hours to about 20 days, about 6 hours to about 19 days, about 1 day to about 19 days, about 3 days to about 19 days, such as about 1, 2, 3, 4, 5, 6, 7, 8, 9, 10, 11, 12, 13, 14, 15, 16, 17, 18, 19 or 20 days.

The concentration of oxytocin is typically at least 0.05 µM, such as at least 0.1 µM or at least 1 µM, such as about 0.05 to about 30 µM, about 0.05 to about 20 µM, about 0.1 to about 20 µM, about 0.5 to about 20 µM, about 1 to about 20 µM, about 5 to about 20 µM, about 5 to about 15 µM or about 10 µM, such as about 0.05, 0.1, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 µM.

The cut flowers are typically exposed to the solution comprising oxytocin at a temperature of about 1 to about 35° C. such as from about 1 to about 25° C., from about 1 to about 20° C., from about 1 to about 15° C., from about 1 to about 10° C., from about 5 to about 10° C., from about 10 to about 15° C., from about 20 to about 25° C., or from about 20 to about 22° C., such as from about 1, 2, 3, 4, 5, 6, 7, 8, 9, 10, 11, 12, 13, 14, 15, 16, 17, 18, 19, 20, 21, 22, 23, 24, 25 or 26° C.

The solution comprising oxytocin may have any pH as long as this does not harm the cut flower. Typically, the pH may be from about 1 to about 9, such as from about 2 to about 8, from about 2 to about 7, from about 2 to about 6, from about 2 to about 5, from about 2 to about 4, from about 3 to about 5, from about 3 to about 4, such as about, 1, 2, 3, 4, 5, 6, 7, 8, or 9.

The solution comprising oxytocin may consist of oxytocin and water, such as tap water. However, it is also possible to add further substances to the solution comprising oxytocin, such as substances commonly added to improve the health and longevity of cut flowers.

As is demonstrated in the experimental section (see Examples 1-3), treating the cut flowers with oxytocin the first time the cut flowers are put into water after harvesting, results in an increased bud opening and/or longevity of the cut flowers. After this pre-treatment with oxytocin, the cut flowers were moved to a home-like setting, i.e. placed at room temperature in regular tap water and the appearance of the cut flowers over time was observed. It was surprisingly found that the cut flowers that had been exposed to oxytocin had an increased longevity and/or increased bud opening. The oxytocin was thus shown to exert its effect even after the cut flowers had been placed in regular tap water without any oxytocin, i.e. when the oxytocin only was used as a pre-treatment.

Instead of, or in addition to, oxytocin, it is possible to use a fragment and/or variant of oxytocin according to SEQ ID NO:2 possessing oxytocin activity,
wherein SEQ ID NO:2 is

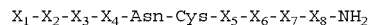

$X_1$-$X_2$-$X_3$-$X_4$-Asn-Cys-$X_5$-$X_6$-$X_7$-$X_8$-$NH_2$ wherein
$X_1$ is selected from the group consisting of Cys and nothing;
$X_2$ is selected from the group consisting of Tyr, Phe, and nothing;
$X_3$ is selected from the group consisting of Ile, Val, Hoph, Phe, Cha, and nothing;
$X_4$ is selected from the group consisting of Gln, Ser, Thr, Cit, Arg, and Daba;
$X_5$ is selected from the group consisting of Pro and nothing;
$X_6$ is selected from the group consisting of Ile, Leu, nothing, Val, Hos, Daba, Thr, Arg, and Cit;
$X_7$ is selected from the group consisting of Gly, nothing, and Ala;
$X_8$ is selected from the group consisting of Gly and nothing;

Examples of such oxytocin fragments or variants are given in SEQ ID NO: 3-24. When such a fragment and/or variant of oxytocin is used, the concentration of said fragment and/or variant may be the same as specified herein for oxytocin. Further, if a combination of oxytocin and fragments and/or variants thereof are used, then the total concentration of oxytocin and the fragment and/or variant thereof may be as specified herein.

The present document is also directed to the use of oxytocin and/or a fragment and/or variant thereof as defined herein for increasing the bud opening and/or longevity of cut flowers.

The cut flowers that are exposed to the solution comprising oxytocin may be any kind of cut flower. For example, the cut flowers may be roses. Other examples of cut flowers that may be exposed to the solution comprising oxytocin and/or a fragment and/or variant thereof as defined herein are tulips, carnations, lilies, asters, orchids, ornamental leaves etc.

The invention will be further described in the following examples, which do not limit the scope of the invention described in the claims.

EXPERIMENTAL SECTION

Example 1: The Effect of Oxytocin on the Survival of Cut Flowers

The stalks of newly delivered roses of the type Upper class were cut (1 cm from the lowest part of the stem) and thereafter the roses were placed in buckets containing water with different doses of oxytocin (For doses see Table 1 and kept in a cold-storage room for 18 days. Four roses were included in each treatment group.

TABLE 1

| Doses of oxytocin uM oxytocin |
| --- |
| 0 |
| 0.1 |
| 0.25 |
| 0.5 |

TABLE 1-continued

| Doses of oxytocin uM oxytocin |
| --- |
| 1 |
| 2.5 |
| 5 |
| 10 |

Thereafter, the roses were moved to a home-like setting with normal room temperature. The stalk of the roses was cut again and the roses were placed in individual vases filled with tap water.

The appearance of the roses was assessed at 4, 9, 15 and 20 days after being moved to the home-like setting according to the criteria demonstrated in Table 2. The assessment criteria were: degree of bud opening (i.e. degree of flower turn-out), degree of drooping (i.e. how bent the stalk was, freshness of the petals, freshness of the sepals and freshness of stem leaves. Each assessment criterion was given a score from 1-5 according to the description. An average score based on all the assessment criteria was also calculated.

TABLE 2

Assessment of the five criteria florescence, drooping, freshness of petals, freshness of sepals.

| Criterion | Score | Assessment | Comments |
| --- | --- | --- | --- |
| Bud opening | 5 | 100% | Fully open |
|  | 4 | 80% |  |
|  | 3 | 60% |  |
|  | 2 | 40% |  |
|  | 1 | 20% |  |
|  | 0 | 0% | Bud |
| Drooping | 5 | 0° | Straight |
|  | 4 | 30° |  |
|  | 3 | 60° |  |
|  | 2 | 90° |  |
|  | 1 | 120° |  |
|  | 0 | 150° | Inflorescence bent 150° |
| Freshness of petals | 5 | 100% | Completely fresh petals |
|  | 4 | 80% |  |
|  | 3 | 60% |  |
|  | 2 | 40% |  |
|  | 1 | 20% |  |
|  | 0 | 0% | Completely dried petals |
| Freshness sepals | 5 | 100% | Completely fresh sepals |
|  | 4 | 80% |  |
|  | 3 | 60% |  |
|  | 2 | 40% |  |
|  | 1 | 20% |  |
|  | 0 | 0% | Completely dried sepals |
| Freshness stem leaves | 5 | 100% | Completely fresh |
|  | 4 | 80% |  |
|  | 3 | 60% |  |
|  | 2 | 40% |  |
|  | 1 | 20% |  |
|  | 0 | 0% | Completely dry/fallen off |

The results show that treatment with oxytocin in doses between 1-10 µmolar concentration affected the composite score as well as all the individual assessments in a positive direction, see FIGS. 1 and 2, respectively.

Experiment 2: The Effect of Oxytocin on the Florescence of Roses of the Type "Furiosa"

The stalks of newly delivered roses of the type Furiosa were cut (1 cm from the lowest part of the stem) and thereafter the roses were placed in buckets containing water with different doses of oxytocin (0, 0.1, 1 and 10 µM) and kept in a cold-storage room for 0.25, 1.3 and 19 days. Nine roses were included in each treatment group.

Thereafter, the roses were moved to a home like setting with normal room temperature. The stalks of the roses were again cut and the roses were placed in individual vases filled with tap water.

The appearance of the roses was assessed at 0, 4, 7, 12, 15, 18 and 20 days according to the criteria demonstrated in Table 2 (see Example 1). The assessment criteria were: degree of bud opening (i.e. degree of flower turn-out), degree of drooping (i.e. how bent the stalk was, freshness of the petals, freshness of the sepals and freshness of the stem leaves. Each assessment criterion was given a score from 1-5 according to the description. An average score based on all the assessment criteria was also calculated.

Figure 3A:
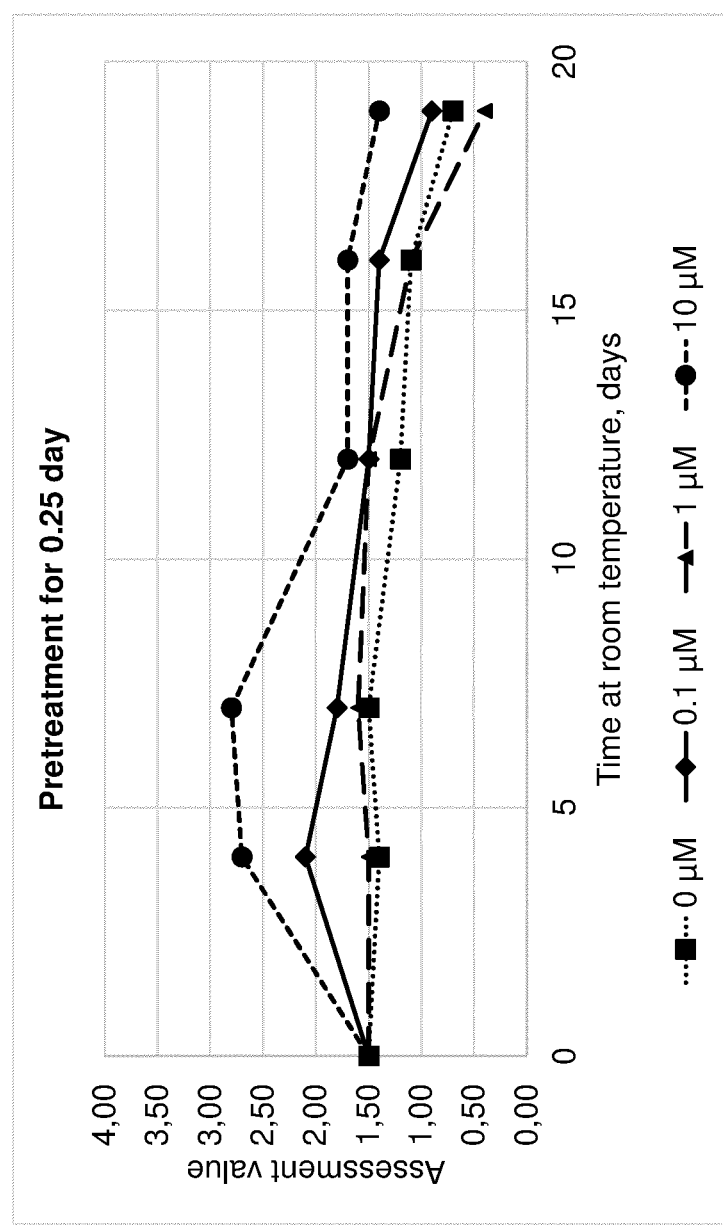
FIGS. 3A-3C show the degree of bud opening in roses of the Furiosa type at home-like setting after pretreatment in a cold room for 0.25, 1 or 3 days with oxytocin in a dose of 0, 0.1, 1 and 10 µM, as described in Example 2.
Figure 3B:
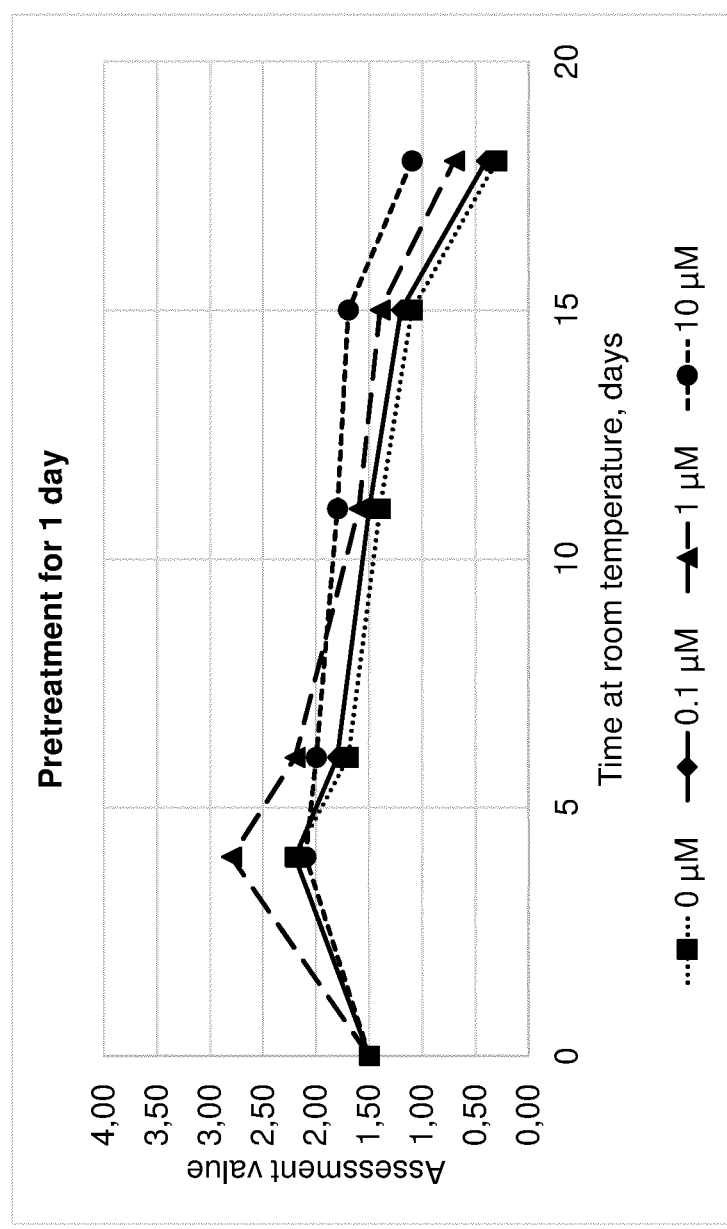
Figure 3C:
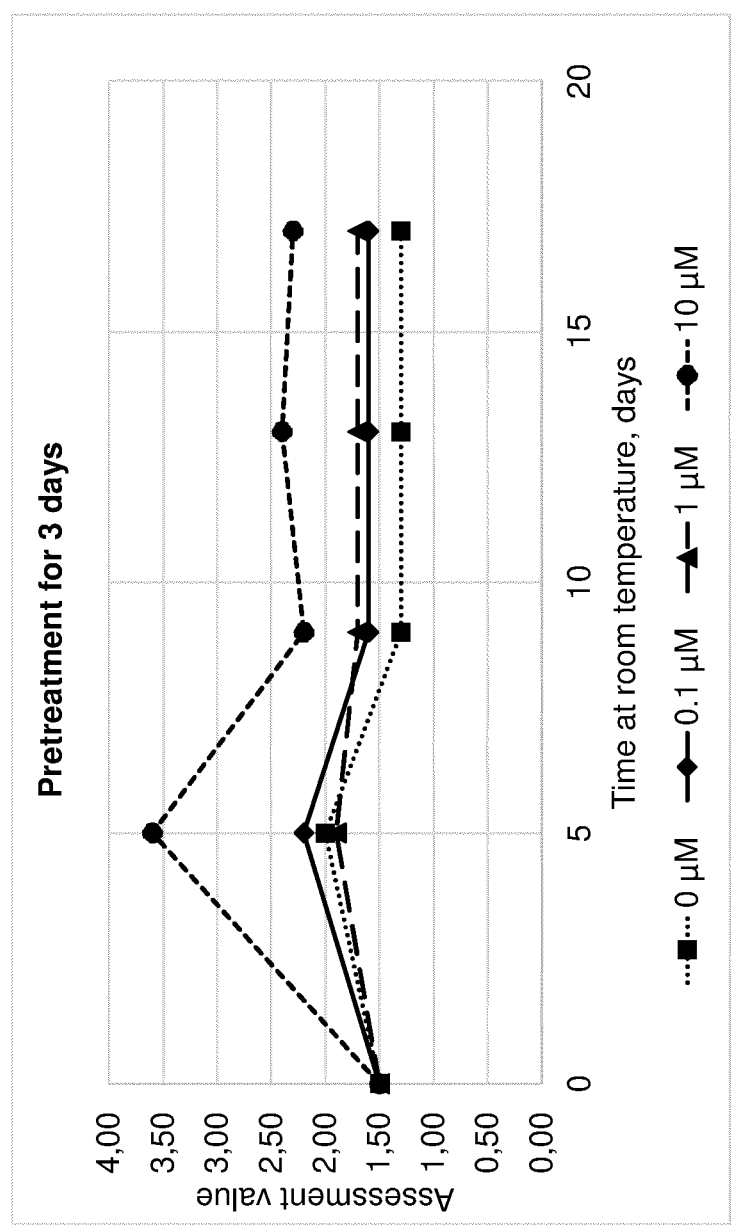
Figure 4:
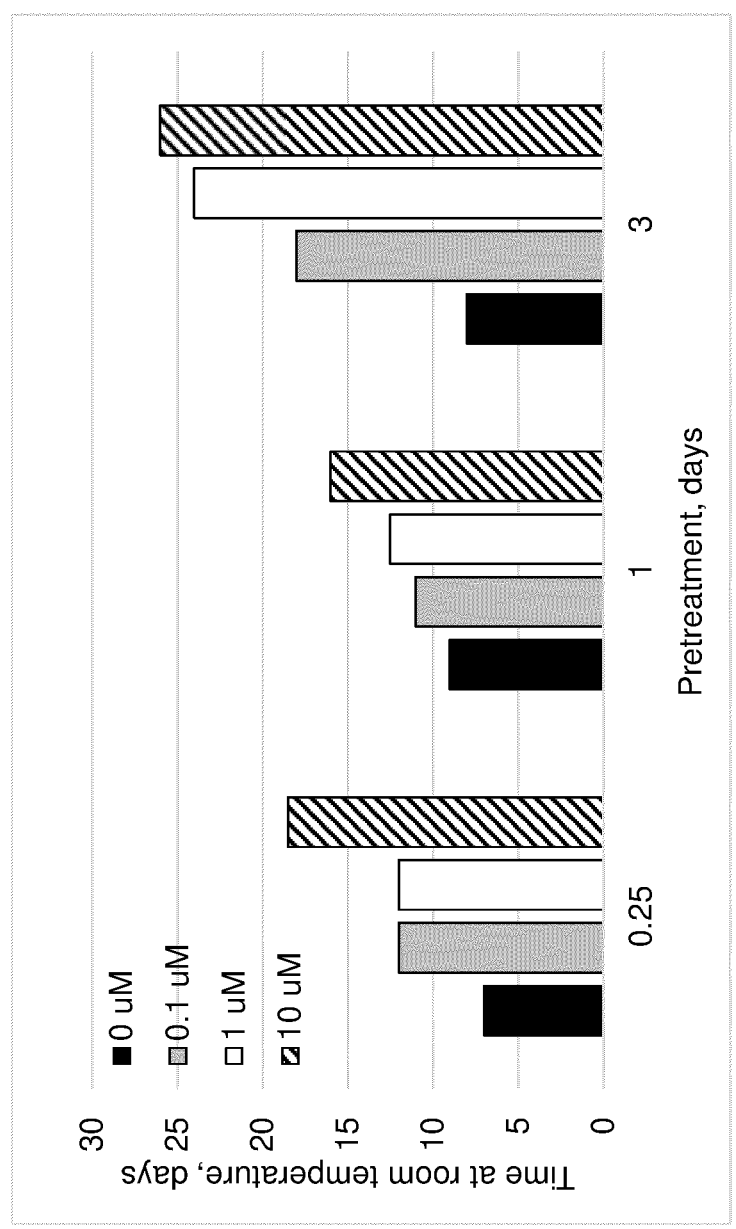
FIG. 4 shows the number of days that roses of the Furiosa type, described in Example 2 and pretreated with oxytocin have a bud opening score above 1.5 (30% of full opening) after being put in tap water and moved to a home-like setting.

The results show that oxytocin, in particular at a dosage of 10 µM, increased the degree of bud opening. The effect was more pronounced after treatment with oxytocin for 3 days than for 6 hours, see FIG. 3. In addition, the duration of time during which the roses kept fresh and attractive increased in response to oxytocin, in particular with 10 µM oxytocin, see FIG. 4.

Example 3: The Effect of Oxytocin on the Survival of Roses of the Type "Belle Rose"

The stalks of newly delivered roses of the type Belle Rose were cut (1 cm from the lowest part of the stem) and thereafter the roses were placed in buckets containing tap water or tap water with different doses of oxytocin (0, 1, 5 and 10 µM in the presence of Chrysal) and kept in a cold-storage room for 3 days. Eight to nine roses were included in each bucket.

Thereafter, the roses were moved to a home like setting with normal room temperature. The stalks of the roses were again cut and the rose bouquets were placed in vases filled with tap water.

The appearance of the roses was assessed at 0, 2, 4, 7 10 and 13 days after being placed in the home like setting according to the criteria shown in Table 2 (see Example 1). The assessment criteria were: degree of bud opening (i.e. degree of flower turn-out), degree of drooping (i.e. how bent the stalk was, freshness of the petals, freshness of the sepals and freshness of the stem leaves. Each assessment criterion was given a score from 1-5 according to the description. An average score based on all the assessment criteria was also calculated.

Figure 5:
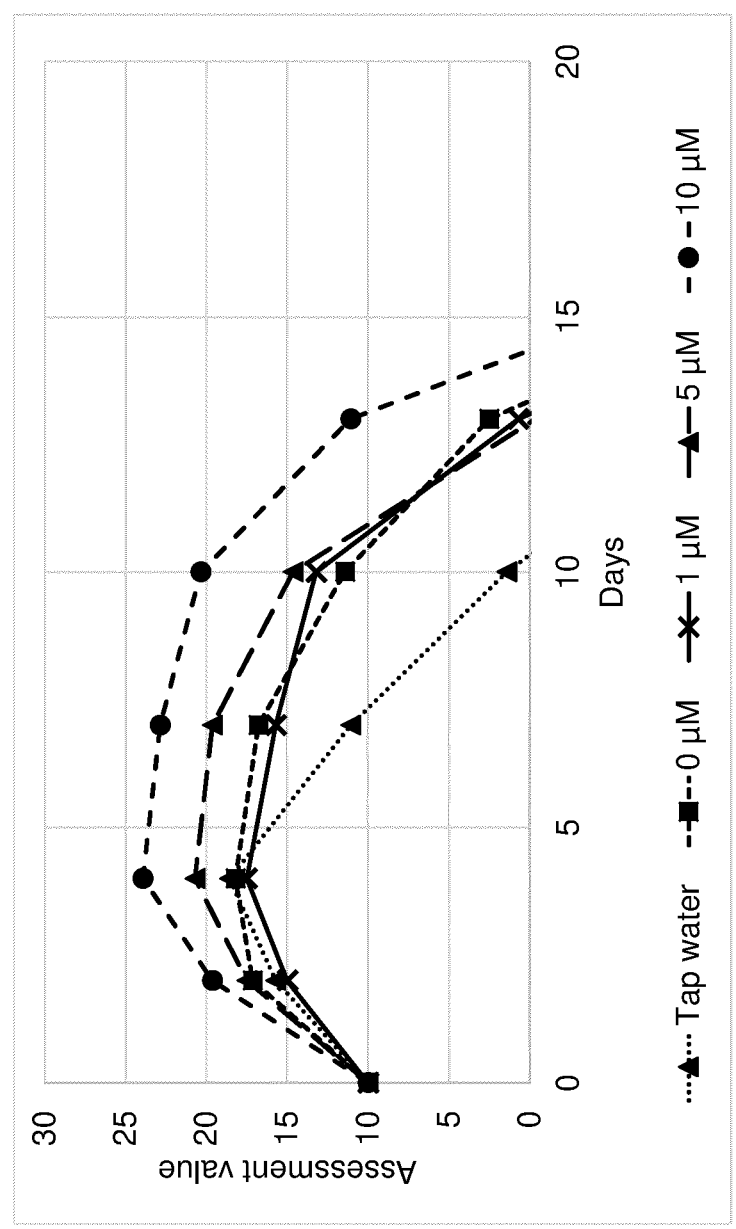
FIG. 5 shows the scores after a visual evaluation of the appearance of bouquets of the type Belle Rose from 0 to 16 days after being put in tap water and moved to a home-like setting after oxytocin pretreatment (according to FIG. 6) in a cold room according to Example 3. 30 points means that all the roses have developed in a nice way, are fresh and stand straight in the vases (i.e. no drooping), 0 points means that the roses have withered so that they would not have been possible to sell. Chrysal is a flower nutrient product often sold together with cut flowers.
Figure 6:
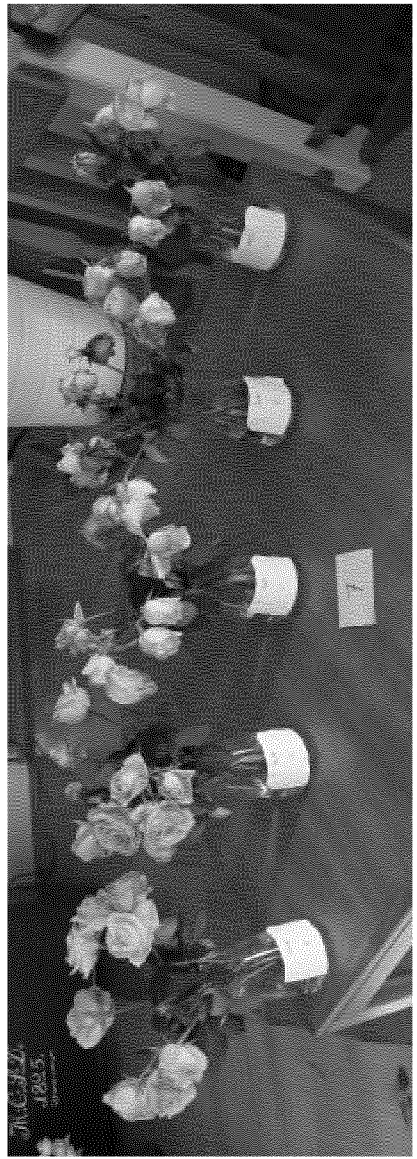
FIG. 6 shows a representative picture of the effects of pretreatment with oxytocin in cold room on roses of the type Belle Rose on day 13 after the flowers were put in fresh tap water and moved to a home-like setting according to Example 3. From left to right: Chrysal+10 µM oxytocin; Chrysal+5 µM oxytocin; Chrysal+1 µM oxytocin; Chrysal; tap water. Chrysal is a flower nutrient product often sold together with cut flowers.

The results show that oxytocin, in particular at a dosage of 10 µM, increased the level of florescence. In addition, the duration of time during which the roses kept fresh and attractive increased in response to oxytocin, in particular at 10 µM oxytocin, see FIGS. 5 and 6.

The invention claimed is:

1. A method for increasing bud opening and/or longevity of a cut flower, said method comprising
exposing an end of a stem of the cut flower to a solution comprising oxytocin, thereby increasing bud opening and/or longevity of the cut flower;
wherein increasing the bud opening is defined as increasing one or more of the following: the number of buds which open or buds opening more fully, and the increase is compared to an identical cut flower wherein an end of a stem of the identical cut flower is not exposed to the solution comprising oxytocin; and/or
wherein increasing longevity is defined as an increase in the time before the cut flower withers and the increase is compared to an identical cut flower wherein an end of a stem of the identical cut flower is not exposed to the solution comprising oxytocin.

2. The method according to claim 1, wherein the concentration of oxytocin is about 0.05 to about 30 μM in the solution comprising oxytocin.

3. The method according to claim 1, wherein the concentration of oxytocin is about 0.05 to about 20 μM in the solution comprising oxytocin.

4. The method according to claim 1, wherein the concentration of oxytocin is about 0.1 to about 20 μM in the solution comprising oxytocin.

5. The method according to claim 1, wherein said cut flower is exposed to said solution comprising oxytocin for a time period of at least 6 hours.

6. The method according to claim 1, wherein the cut flower is exposed to said solution comprising oxytocin at a temperature of about 1 to about 25° C.

7. The method according to claim 1, wherein said solution comprising oxytocin has a pH of about 1 to about 9.

8. The method according to claim 1, wherein said cut flower is a rose.

9. The method according to claim 1, wherein said oxytocin consists of one or more of the following:
(i) oxytocin in accordance with SEQ ID NO:1, or a fragment thereof, or
(ii) a variant of oxytocin according to SEQ ID NO:2 possessing oxytocin activity, or a fragment thereof, wherein SEQ ID NO:2 is $$X_1-X_2-X_3-X_4-Asn-Cys-X_5-X_6-X_7-X_8-NH_2$$

wherein
$X_1$ is selected from the group consisting of Cys and nothing;
$X_2$ is selected from the group consisting of Tyr, Phe, and nothing;
$X_3$ is selected from the group consisting of Ile, Val, Hoph, Phe, Cha, and nothing;
$X_4$ is selected from the group consisting of Gln, Ser, Thr, Cit, Arg, and Daba;
$X_5$ is selected from the group consisting of Pro and nothing;
$X_6$ is selected from the group consisting of Ile, Leu, nothing, Val, Hos, Daba, Thr, Arg, and Cit;
$X_7$ is selected from the group consisting of Gly, nothing, and Ala;
$X_8$ is selected from the group consisting of Gly and nothing.

10. The method according to claim 1, wherein said oxytocin consists of oxytocin in accordance with SEQ ID NO:1, or a fragment thereof.

11. The method according to claim 1, wherein said oxytocin consists of the variant of oxytocin according to SEQ ID NO:2 possessing oxytocin activity, or a fragment thereof.

12. The method according to claim 1, wherein said solution comprising oxytocin is an aqueous solution.

13. The method according to claim 12, wherein said aqueous solution comprises no further solvent in addition to water.

14. The method according to claim 1, wherein the concentration of oxytocin is about 5 µM to about 15 µM in the solution comprising oxytocin.

15. The method according to claim 1, wherein said cut flower is exposed to said solution comprising oxytocin for a time period of about 6 hours to about 30 days.

16. The method according to claim 1, wherein the cut flower is exposed to said solution comprising oxytocin at a temperature of about 20° C. to about 25° C.

17. The method according to claim 1, wherein said solution comprising oxytocin has a pH of about 2 to about 5.

* * * * *